(12) United States Patent
Rüter

(10) Patent No.: US 6,406,496 B1
(45) Date of Patent: Jun. 18, 2002

(54) HUMERUS HEAD PROSTHESIS

(75) Inventor: Axel Rüter, Neusäss (DE)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/600,356

(22) PCT Filed: Jan. 15, 1999

(86) PCT No.: PCT/EP99/00209

§ 371 (c)(1),
(2), (4) Date: Jul. 14, 2000

(87) PCT Pub. No.: WO99/37254

PCT Pub. Date: Jul. 29, 1999

(30) Foreign Application Priority Data

Jan. 22, 1998 (DE) .................... 298 00 975 U

(51) Int. Cl.[7] .................................................. A61F 2/40
(52) U.S. Cl. .................. 623/19.14; 623/19.11
(58) Field of Search ............... 623/23.33, 19.12, 623/19.11, 19.14

(56) References Cited

FOREIGN PATENT DOCUMENTS

| DE | 19614949 A1 | 10/1997 |
|---|---|---|
| EP | 0191182 A1 | 8/1986 |
| EP | 0423064 A1 | 4/1991 |
| EP | 0466638 A1 | 1/1992 |
| FR | 2726994 | 5/1996 |
| WO | WO 96/36300 | 11/1996 |
| WO | WO 97/39693 | 10/1997 |

*Primary Examiner*—Corrine McDermott
*Assistant Examiner*—Thomas C. Barrett
(74) *Attorney, Agent, or Firm*—Townsend and Townsend and Crew LLP

(57) ABSTRACT

A humerus head prosthesis including a head and a shaft. A hollow quiver which has one or more openings in the jacket is arranged at the shaft proximally and below the head. The quiver is located at the level of the anatomical position of the tubercles and laterally at the shaft. The jacket openings are formed as threaded bores for screws.

4 Claims, 1 Drawing Sheet

HUMERUS HEAD PROSTHESIS

BACKGROUND OF THE INVENTION

1. Field of the Invention

The invention relates to a humerus head prosthesis.

2. Description of the Prior Art

A humerus head prosthesis or shoulder prosthesis of this kind is known from the prior art. It has a head and a shaft. The head, which corresponds substantially to a spherical segment, can be releasably connected to the shaft via a neck. It has an eccentric bore for the neck. In humerus head prostheses there is the problem of the bone integration of the tubercles at the prosthesis. The previously known humerus head prosthesis offers no practicable and reliable help for this.

SUMMARY OF THE INVENTION

The object of the present invention is therefore to provide a humerus head prosthesis with an improved integration possibility of the tubercles.

The present invention provides a humerus head prosthesis that includes a hollow quiver arranged at the shaft and facilitates the integration of the tubercles at the prosthesis. It can be filled with bone shavings or bone splinters, with an ossification and a connection to or of the tubercles through the jacket openings being possible. In many cases of a shoulder lesion the tendon is still grown on at the tubercles, with the detachment having taken place in the bone. The tendons with the tubercles can then again be secured to the humerus head prosthesis and integrated via the ossification.

The jacket openings of the quiver also afford a possibility for the exact positioning and temporary securing of the tubercles at the anatomically correct location. For this purpose it is also provided in accordance with the invention that the quiver is arranged subcapitally at the level of the anatomical location of the tubercles and laterally at the shaft. The proximally lying filling-in opening facilitates the introduction of the bone shavings. The funnel-like quiver shape also facilitates this, with the funnel shape additionally assisting the anatomically correct positioning of the tubercles and in addition offering more bone matter in the proximal region for the growing on than in the distal region in an anatomically favorable manner.

In a particularly advantageous manner at least a portion of the jacket openings is provided with screw threads, which permit an exact positioning of the tubercles by means of bone screws. For improving the thrift it is advantageous in this to provide the threaded bore with a metric thread in order to be able to use economical standard screws with compression collars.

DETAILED DESCRIPTION OF SPECIFIC EXEMPLARY EMBODIMENTS

Figure 1:
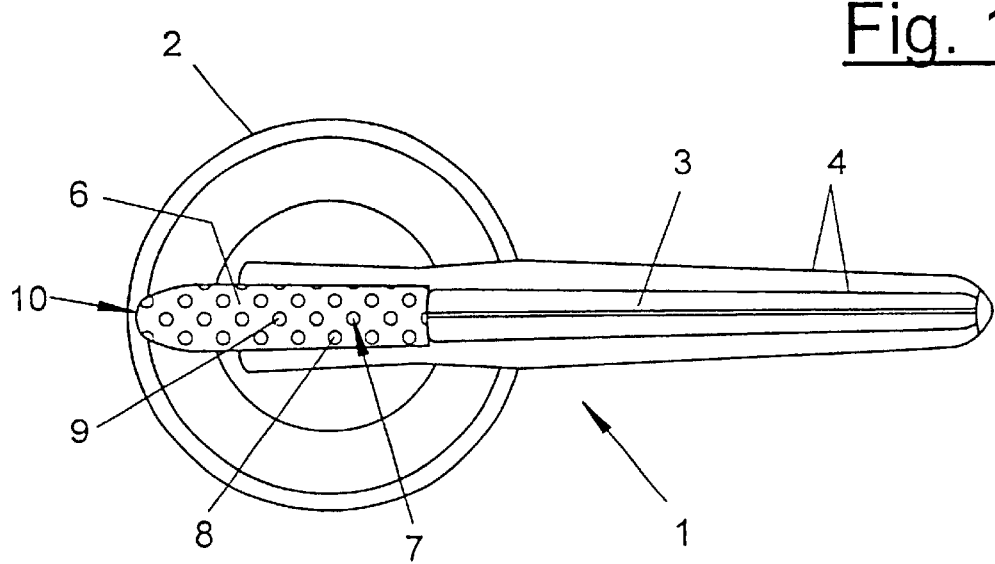
FIG. 1 is a humerus head prosthesis in a bottom view as seen from the distal end.
Figure 2:
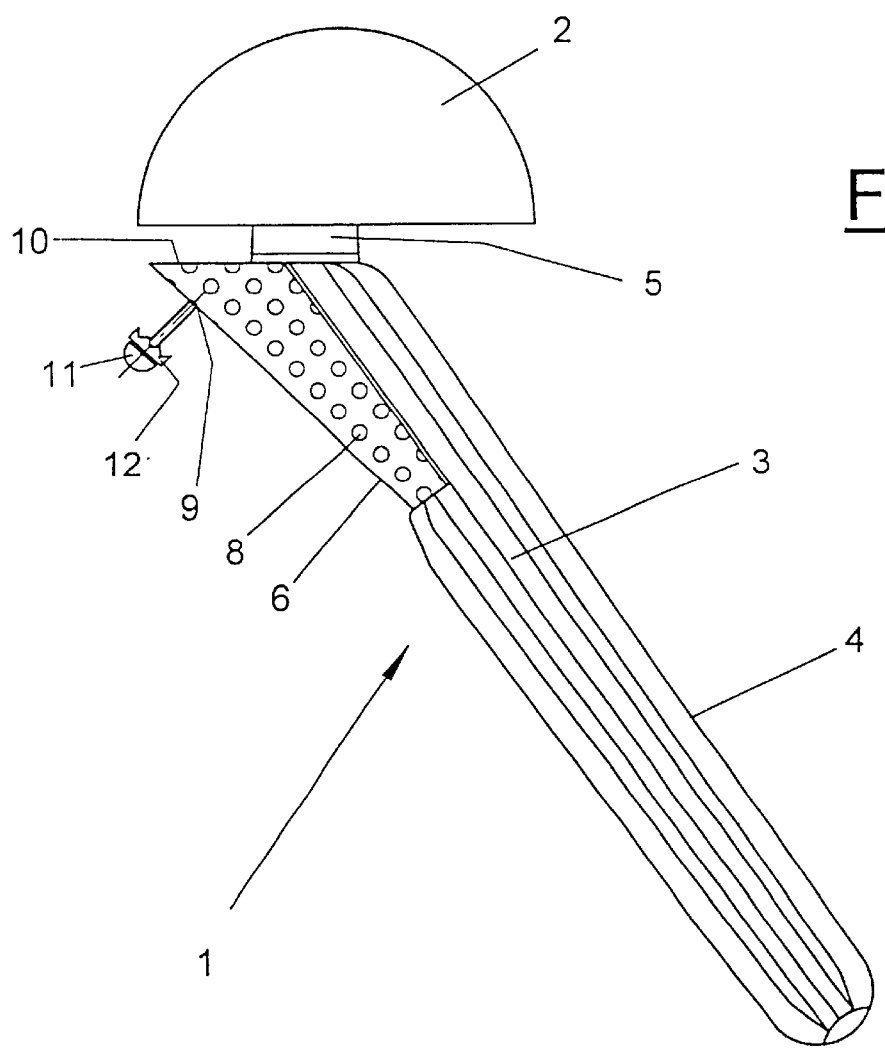
FIG. 2 is a side view of the prosthesis of FIG. 1.

The humerus head prosthesis (1) consists of a substantially hemispherical head (2) and a shaft (3), which are connected via a neck (5). The connection between the neck (5) and the head (2) can be releasable. The humerus head prosthesis (1) can have any desired suitable shape in the shaft and head region.

A hollow quiver (6) is arranged laterally at the prosthesis shaft (3) for the reception of bone shavings, bone splinters or the like. The quiver (6) is located subcapitally at the level of the anatomical location of the tubercles and preferably terminates at the proximal end flush with the prosthesis shaft (3). In the quiver region the prosthesis shaft (3) can have a flattening or a cut-out. This facilitates on the one hand the attaching of the quiver (6) and increases the quiver volume on the other hand.

The humerus head prosthesis (1) and the quiver (6) consist of a body compatible inert material, e.g. titanium. The quiver (6) has a vaulted shape and is connected with its edges to the shaft (3) in a suitable way, e.g. through welding or the like. In this, guides, centerings and other positioning and securing aids can be present.

The hollow quiver (6) has a funnel shape which widens proximally and has a filling-in opening (10) proximally. Through this the bone shavings can be filled in from the proximal direction. The head (2) can be removed from the neck (5) for this. A filling in beneath the placed on head is also possible where appropriate.

The quiver has a jacket with one or more openings (8). The latter can be circular and have any other shape desired and can be punched free out of the jacket or be manufactured in another suitable manner. The quiver jacket can furthermore have one or more threaded bores (9). In this a portion of or all the openings (8) can be formed as threaded bores (9). The threaded bores (9) are preferably located in the lateral jacket area.

The threaded bores have a metrical thread and can receive standard screws (11). Otherwise, however, different kinds of screws with other threads can also be used. It is also possible to use screws with self-cutting threads or sheet metal lamina threads for connecting with simple openings (8).

In the preferred embodiment the screws (11) also have a compression collar (12). The pot-like compression collar (12) has tips which project at the edge side, which distribute the pressing force better and which ensure a secure screw holding.

The humerus head prosthesis (1) in accordance with the invention enables the exact integration of detached tubercles (non-illustrated). For this, one or more screws (11) are inserted via suitable passage bores into the tubercles and are fixed at the openings (8) or threaded bores (9) of the quiver (6) respectively.

The humerus head prosthesis (1) can otherwise have any further design features desired. The shaft (3) has e.g. one or more longitudinally extending ribs (4) for fixing in the humerus. The head (2) can have an eccentric reception opening for the neck (5). In addition it can have turned out hollowings and other cut-outs to save material.

Modifications of the illustrated embodiment are possible in various ways. Thus the hollow quiver can have any other desired shape and position at the prosthesis shaft (3). In addition the tubercles can be secured at the quiver (6) in a suitable manner other than by screws. The openings (8) or threaded bores (9) respectively can be uniformly or non-uniformly distributed at the quiver jacket in the form shown. Their number and arrangement can vary in any desired manner.

What is claimed is:

1. A humerus head prosthesis comprising a head, a shaft and a holder for filling-in bone splinters, wherein the holder is arranged subcapitally at the level of an anatomic location of tubercles and laterally at the shaft and terminates at a proximal end flush with the shaft, and wherein the holder has a filling-in opening proximally and at least one additional opening, wherein the prosthesis comprises at least one bone screw that fits into at least part of at least one additional opening of the holder for fixing the tubercles to the holder.

2. A humerus head prosthesis in accordance with claim 1, wherein the holder has a funnel shape that widens proximally.

3. A humerus head prosthesis in accordance with claim 1, wherein the holder has at least one threaded bore.

4. A humerus head prosthesis in accordance claim 3, wherein the at least one threaded bore has a metrical thread for reception of standard screws with compression collars.

* * * * *